United States Patent
Cheng et al.

(10) Patent No.: US 10,254,267 B2
(45) Date of Patent: Apr. 9, 2019

(54) WATER QUALITY SENSOR SUITABLE FOR AUTOMATED PRODUCTION

(71) Applicant: SOLTEAM OPTO, INC., Taoyuan (TW)

(72) Inventors: Chih-Teng Cheng, Taoyuan (TW); Fu-Min Liang, Taoyuan (TW); Chin-Feng Chen, Taoyuan (TW)

(73) Assignee: SOLTEAM OPTO, INC., Taoyuan (TW)

( * ) Notice: Subject to any disclaimer, the term of this patent is extended or adjusted under 35 U.S.C. 154(b) by 103 days.

(21) Appl. No.: 15/431,226

(22) Filed: Feb. 13, 2017

(65) Prior Publication Data

US 2017/0234848 A1  Aug. 17, 2017

(30) Foreign Application Priority Data

Feb. 16, 2016 (TW) ............................... 105104472 A

(51) Int. Cl.
*G01N 21/17* (2006.01)
*G01N 33/18* (2006.01)
(Continued)

(52) U.S. Cl.
CPC .......... *G01N 33/18* (2013.01); *A47L 15/4297* (2013.01); *G01N 21/17* (2013.01); *G01N 21/534* (2013.01)

(58) Field of Classification Search
CPC ........ A61M 5/20; G01H 17/00; G01M 7/025; G01N 29/12; G01N 21/534; G01N 21/8507; G01N 21/532; G01N 21/82; G01N 33/18; A47L 15/4297; A47L 2401/10; D06F 2202/02
See application file for complete search history.

(56) References Cited

U.S. PATENT DOCUMENTS 6,771,373 B2 * 8/2004 Schenkl .............. A47L 15/4297
356/442
7,226,491 B2 * 6/2007 Choi ........................ F01P 11/14
73/114.68

(Continued)

FOREIGN PATENT DOCUMENTS

DE  102007016215 A1 * 10/2007 ......... A47L 15/4297
DE  102006041274 A1 *  3/2008 ......... A47L 15/4297
(Continued)

*Primary Examiner* — David A Rogers
(74) *Attorney, Agent, or Firm* — Muncy, Geissler, Olds & Lowe, P.C.

(57) ABSTRACT

A water quality sensor includes a housing having two hollow protruding portions, and a sensing module including a circuit board mounted inside the housing and having two positioning plates respectively positioned in the two hollow protruding portions, two identical connectors respectively mounted on the two positioning plates of the circuit board in reversed directions with a phase difference of 180 degrees therebetween, and a light emitter and a light receiver respectively mounted in the connectors to face toward each other for water quality detection. Thus, the invention allows the implementation of automated assembly to replace manual assembly, reducing the risk of human error, saving much labor and production costs, improving product quality and increasing product yield.

9 Claims, 10 Drawing Sheets

(51) Int. Cl.
*A47L 15/42* (2006.01)
*G01N 21/53* (2006.01)

(56) References Cited

U.S. PATENT DOCUMENTS

| | | | | |
|---|---|---|---|---|
| 7,397,564 | B2* | 7/2008 | Diez Garcia | D06F 39/004 250/343 |
| 8,654,337 | B2* | 2/2014 | Wu | G01N 21/53 356/213 |
| 8,707,808 | B2* | 4/2014 | Kovacic | G01D 11/30 165/11.1 |
| 8,883,079 | B2* | 11/2014 | Clark | G01N 21/77 422/82.05 |
| 9,671,338 | B1* | 6/2017 | Wu | G01N 21/49 |
| 9,709,505 | B2* | 7/2017 | Choi | G01N 21/85 |
| 2001/0002542 | A1* | 6/2001 | Sasano | D06F 39/004 68/12.02 |
| 2003/0142316 | A1* | 7/2003 | Schenkl | A47L 15/4297 356/442 |
| 2003/0197868 | A1* | 10/2003 | Durfee | G01N 21/534 356/442 |
| 2007/0188763 | A1* | 8/2007 | Schenkl | A47L 15/4297 356/436 |
| 2008/0021631 | A1* | 1/2008 | Busch | B01D 53/88 701/114 |
| 2008/0053256 | A1* | 3/2008 | Kovacic | G01D 11/245 73/866.5 |
| 2009/0231581 | A1* | 9/2009 | Han | A47L 15/0018 356/341 |
| 2012/0002206 | A1* | 1/2012 | Giordano | A47L 15/4297 356/441 |
| 2012/0090654 | A1* | 4/2012 | Bewley, Jr. | A47L 15/4297 134/56 D |
| 2013/0016354 | A1* | 1/2013 | Wu | G01N 21/53 356/441 |
| 2013/0278921 | A1* | 10/2013 | Choi | G01N 21/85 356/51 |
| 2014/0017143 | A1* | 1/2014 | Clark | G01N 21/77 422/402 |
| 2016/0209346 | A1* | 7/2016 | Brondum | G01N 27/07 |
| 2016/0370287 | A1* | 12/2016 | Barnes | G01N 21/05 |
| 2018/0008116 | A1* | 1/2018 | Durham | A47L 15/0031 |

FOREIGN PATENT DOCUMENTS

| | | | | |
|---|---|---|---|---|
| DE | 102006052892 | A1 * | 5/2008 | A47L 15/4297 |
| DE | 102010038689 | A1 * | 2/2012 | A47L 15/4242 |
| EP | 0748891 | A1 * | 12/1996 | A47L 15/4297 |
| EP | 2004031 | B1 * | 9/2016 | A47L 15/4287 |
| WO | WO 2010085736 | A1 * | 7/2010 | G01N 21/532 |
| WO | WO 2012135457 | A1 * | 10/2012 | A47L 15/4297 |

* cited by examiner

WATER QUALITY SENSOR SUITABLE FOR AUTOMATED PRODUCTION

This application claims the priority benefit of Taiwan patent application number 105104472, filed on Feb. 16, 2016.

BACKGROUND OF THE INVENTION

1. Field of the Invention

The present invention relates to water quality sensor technology and more particularly, to a water quality sensor suitable for automated production to achieve enhanced production efficiency and to effectively reduce the manufacturing costs, which comprises a housing, a sensing module comprising a circuit board mounted inside the housing, two identical connectors mounted on the circuit board in reversed directions with a phase difference of 180 degrees therebetween, and a light emitter and a light receiver respectively mounted in the connectors to face toward each other for water quality detection.

2. Description of the Related Art

With the continuous progress in electronic technology, many easy-to-use household electrical appliances have been continuously created. In our daily lives, we use different household electrical appliances to handle different jobs rapidly, saving much labor and time. Many household appliances such as washing machines, dishwashers, and the like are designed for use with water and a cleaning fluid or detergent to achieve cleaning. Thus, we can use these household appliances to wash clothes, dishes, kitchen utensils, etc., instead of hand washing.

Further, when washing some objects in an electric washing machine, dust, debris and other impurities in the objects and the applied cleaning fluid or detergent can cause an increase in the turbidity of the applied water. Thus, the cleaning operation must be repeated several times until the objects to be cleaned are well cleaned. Most electric washing appliances are equipped with a water quality sensor to detect the turbidity of the applied water so that the control system can determine the cleaning mode according to the detected turbidity, enhancing the effectiveness of washing and achieving the purpose of energy saving. Further, water quality sensors are often installed in rivers or water supply areas where water is supplied to meet the needs of people's livelihoods. However, conventional water quality sensors are expensive and commonly designed for industrial applications, in consequence, water quality sensors are not popularly used in houses. Therefore, how to reduce the production cost of water quality sensors has been a big problem for manufacturers.

FIG. 10 illustrates a water quality sensor according to the prior art. According to this design, the water quality sensor comprises a housing (not shown), and a sensing module A mounted in the housing. The sensing module A comprises a circuit substrate A1, which comprises two arms A11 arranged in parallel, a notch A12 located on a front end of each arm A11 and a hook hole A13 located on an opposing rear end of each arm A11, a positioning block A2, which comprises two extension portions A21, a receptacle A211 located on each extension portion A21 of the positioning block A2, a positioning rod A22 located at one end of each extension portion A21 and a hook block A23 located at an opposite end of each extension portion A21, a light emitter A3 mounted in the receptacle A211 at one extension portion A21, and a light receiver A4 mounted in the receptacle A211 at the other extension portion A21. When mounting the positioning block A2 on the circuit substrate A1, tilt the positioning block A2 forward by an angle to force the positioning rods A22 into engagement with the respective notches A12 at the respective arms A11, and then impart a downward pressure to the positioning block A2 to force the two hook blocks A23 into engagement with the respective hook holes A13 of the circuit substrate A1.

The assembly process of the aforesaid prior art water quality sensor needs to be performed by labor, not suitable to automated production. In recent years, the labor and operating costs in the manufacturing industry keep increasing. Further, the additional costs associated with poor manual assembly result in a high rate (about 49%) of the manual assembly cost in the total production cost. In the assembly process of the aforesaid prior art design, mounting the positioning block A2 on the circuit substrate A1 needs to tilt the positioning block A2 forward by an angle to force the positioning rods A22 into engagement with the respective notches A12 at the respective arms A11. This procedure cannot be performed using an automatic plug-in. The manual assembly process to install the positioning block A2 in the circuit substrate A1 wastes much labor and time, resulting in poor production efficiency. Further, the positioning block A2 has a complicated structure, and thus, the related mold designing and manufacturing costs are increased. Therefore, there is a strong demand for a water quality sensor that is suitable for automated product to improve the production efficiency and to reduce to manufacturing cost.

SUMMARY OF THE INVENTION

The present invention has been accomplished under the circumstances in view. It is therefore the main object of the present invention to provide a water quality sensor, which allows the implementation of automated assembly to replace manual assembly, reducing the risk of human error, saving much labor and production costs, improving product quality and increasing product yield.

To achieve this and other objects of the present invention, a water quality sensor comprises a housing and a sensing module. The housing comprises a body shell and a cover. The body shell comprises two hollow protruding portions extended from a back side thereof, an opening located on an opposite front side thereof and an accommodation chamber defined therein in communication with the opening. The cover is capped on the body shell to close the opening. The sensing module comprises a circuit board mounted in the accommodation chamber of the body shell with two positioning plates thereof respectively positioned in the hollow protruding portions of the body shell, two connectors respectively mounted on the positioning plates of the circuit board in reversed directions with a phase difference of 180 degrees therebetween, a light emitter mounted in one connector, and a light receiver mounted in the other connector with the light-receiving surface thereof facing toward the light-emitting surface of the light emitter. The mold sharing design of the connectors of the sensing module does not need to prepare multiple molds for enabling the connectors to mate with the light emitter and the light receiver, saving one half the mold cost, facilitating automatic production, improving the production speed and efficiency, and reducing the manufacturing costs.

Further, the circuit board comprises a plurality of via holes located on each positioning plate and arranged in a line, two position-limiting holes of different diameters respectively located on each positioning plate at opposing front and rear sides relative to the via holes on the respective positioning plate, and two retaining notches respectively located on two opposite lateral sides of each positioning plate. Further, each connector comprises a recessed chamber adapted for accommodating the light emitter or the light receiver, two positioning pins of different diameters respectively mounted in the respective position-limiting holes on one respective positioning plate of the circuit board, and two hook members respectively hooked in the retaining notches on the respective positioning plate of the circuit board.

Subject to the design that the two positioning pins of each connector of the sensing module have different diameters fitting the respective position-limiting holes on each positioning plate of the circuit board, the two connectors can be accurately installed in the circuit board with a phase difference of 180 degrees therebetween, avoiding an installation error that can lead to an operational failure of the light emitter and the light receiver.

Preferably, the body shell of the housing further comprises a convex rib disposed inside the accommodation chamber and spaced between the two hollow protruding portions at different distances; the circuit board of the sensing module further comprises an engaging groove disposed between the two positioning plates and forced into engagement with the convex rib of the body shell of the housing. The mating design between the engaging groove of the circuit board and the convex rib of the body shell prevents a mounting error between the circuit board and the body shell, achieving a foolproof effect.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
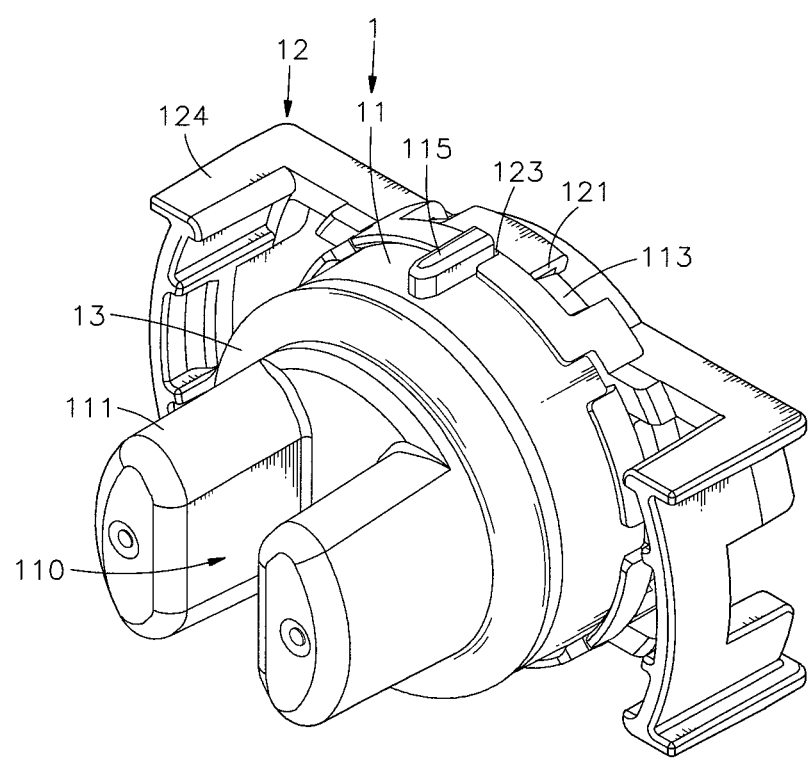
FIG. 1 is an oblique front elevational view of a water quality sensor in accordance with the present invention.
Figure 2:
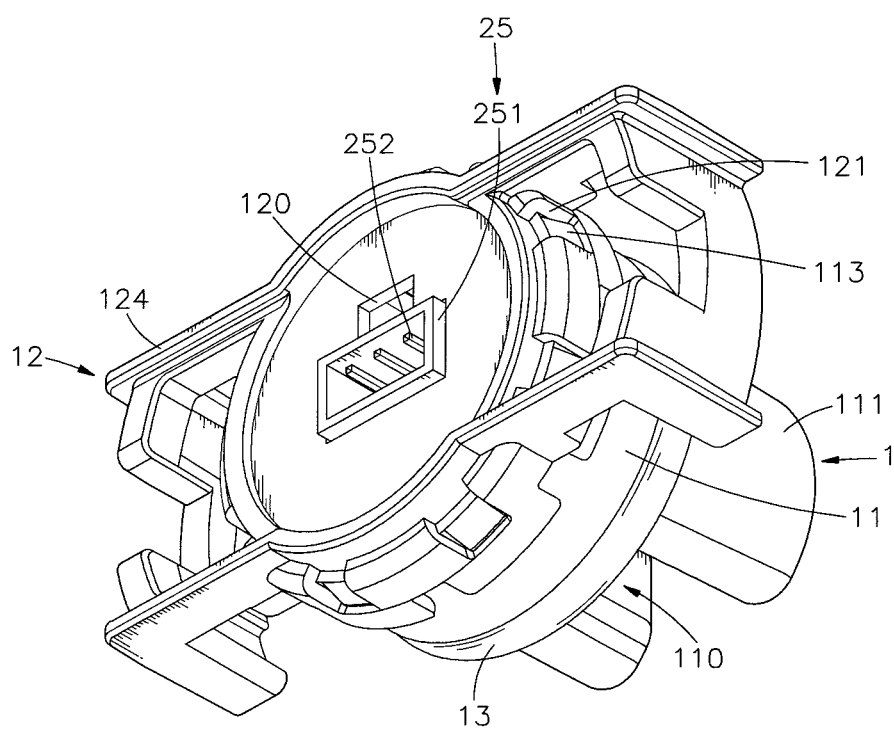
FIG. 2 is an oblique rear elevational view of the water quality sensor in accordance with the present invention.
Figure 3:
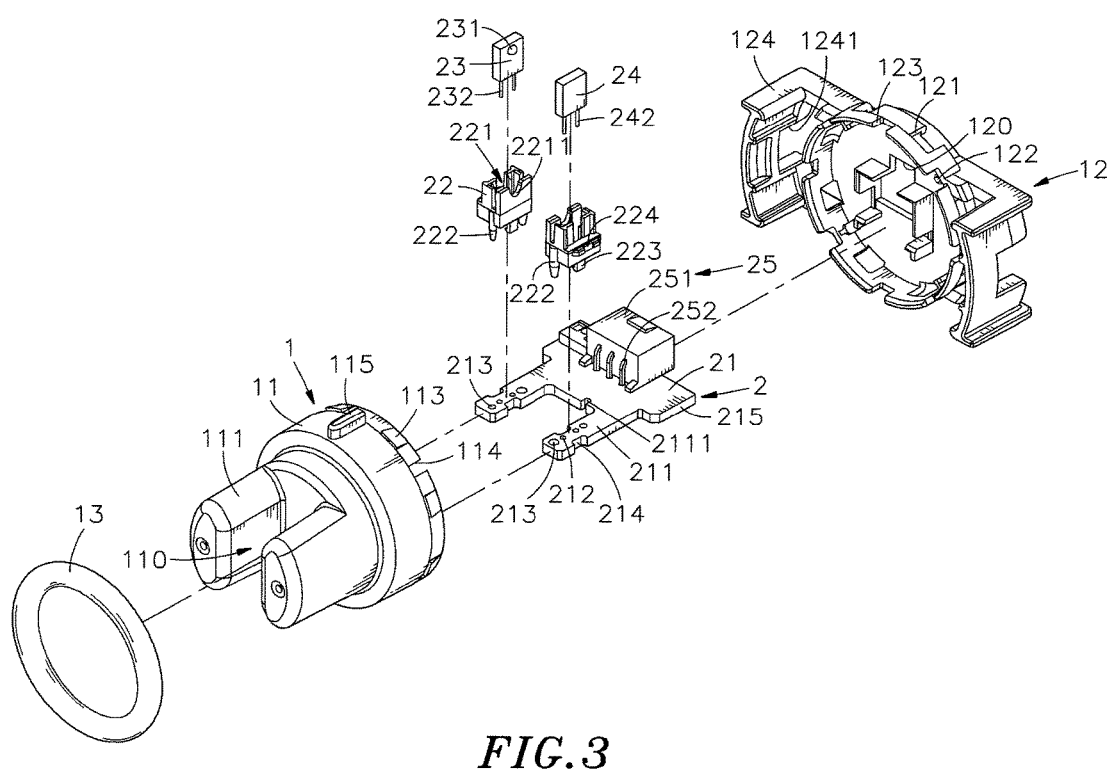
FIG. 3 is an exploded view of the water quality sensor in accordance with the present invention.
Figure 4:
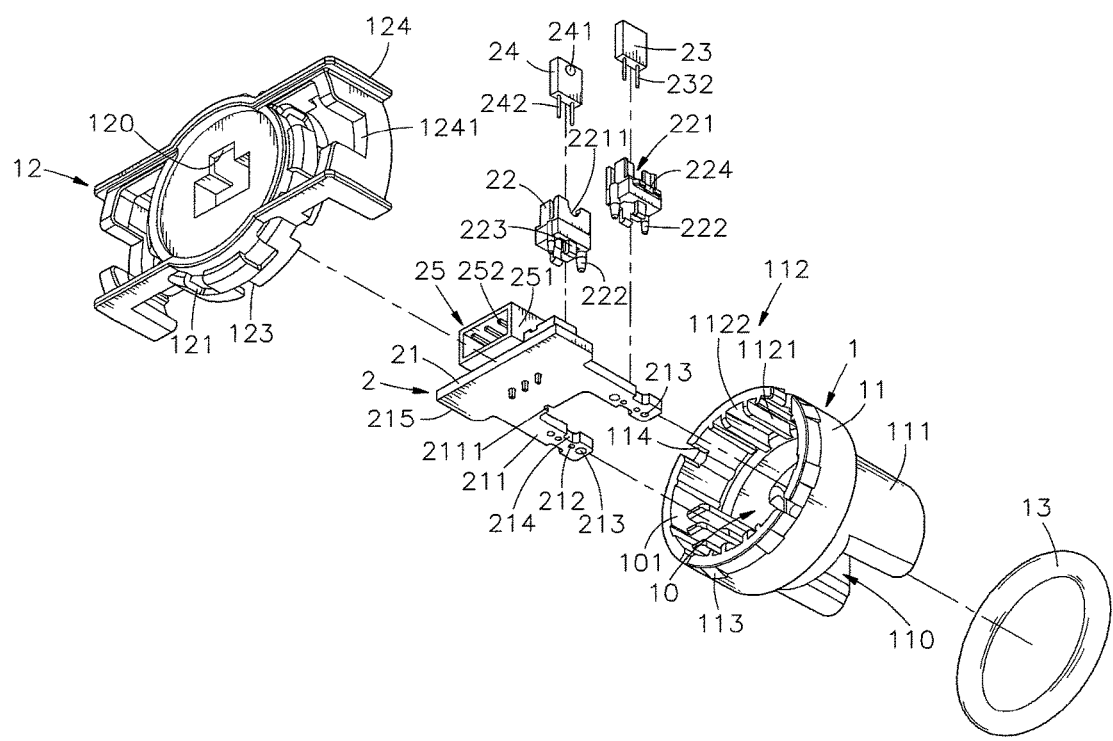
FIG. 4 is another exploded view of the water quality sensor in accordance with the present invention when viewing from another angle.
Figure 5:
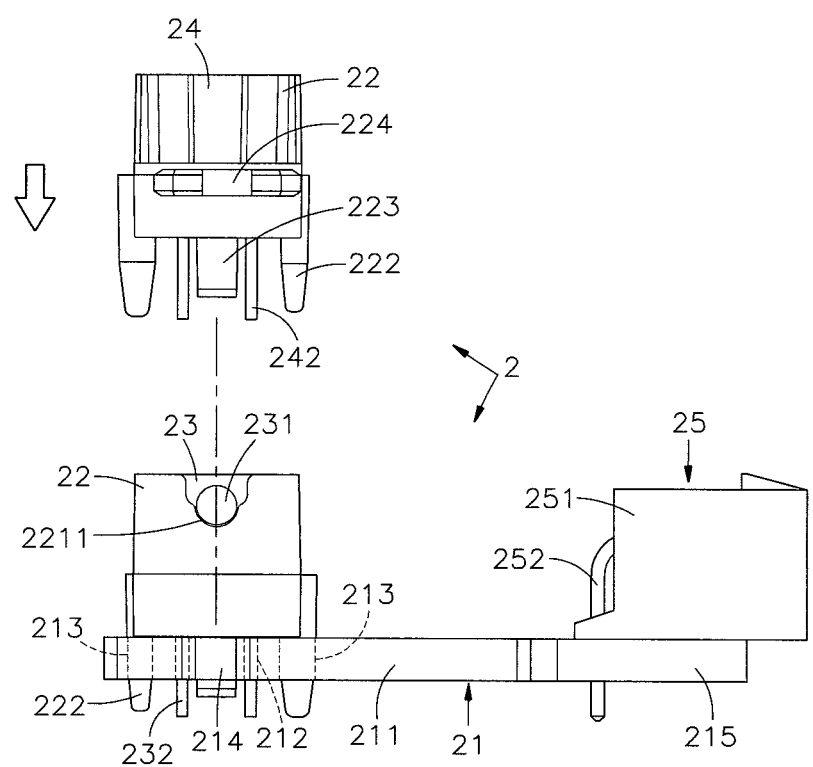
FIG. 5 is a schematic side view of a part of the present invention, illustrating the sensing module assembly process of the water quality sensor.
Figure 6:
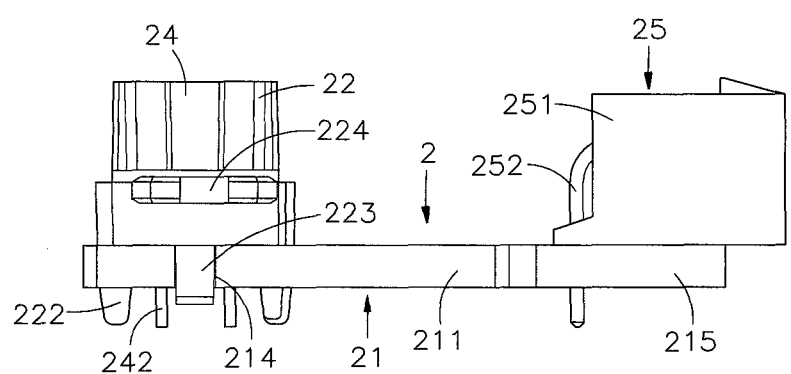
FIG. 6 corresponds to FIG. 5, illustrating the sensing module assembled.

Referring to FIGS. 1-4, a water quality sensor in accordance with the present invention is shown. The water quality sensor comprises a housing 1 and a sensing module 2.

The housing 1 comprises a body shell 11 made of a light transmissive material, a cover 12, and a waterproof gasket 13. The body shell 11 comprises two hollow protruding portions 111 extended from a back wall thereof in a same direction, an open passageway 110 defined between the two hollow protruding portions 111, an accommodation chamber 10 defined therein, and an opening 101 located on a front side thereof opposite to the hollow protruding portions 111 and disposed in communication with the accommodation chamber 10. The cover 12 is fastened to the body shell 11 to cover the opening 101, having a slot 120 cut through opposing front and back walls thereof. The waterproof gasket 13 is mounted around the hollow protruding portion 111 and abutted against the back wall of the body shell 11.

Figure 7:
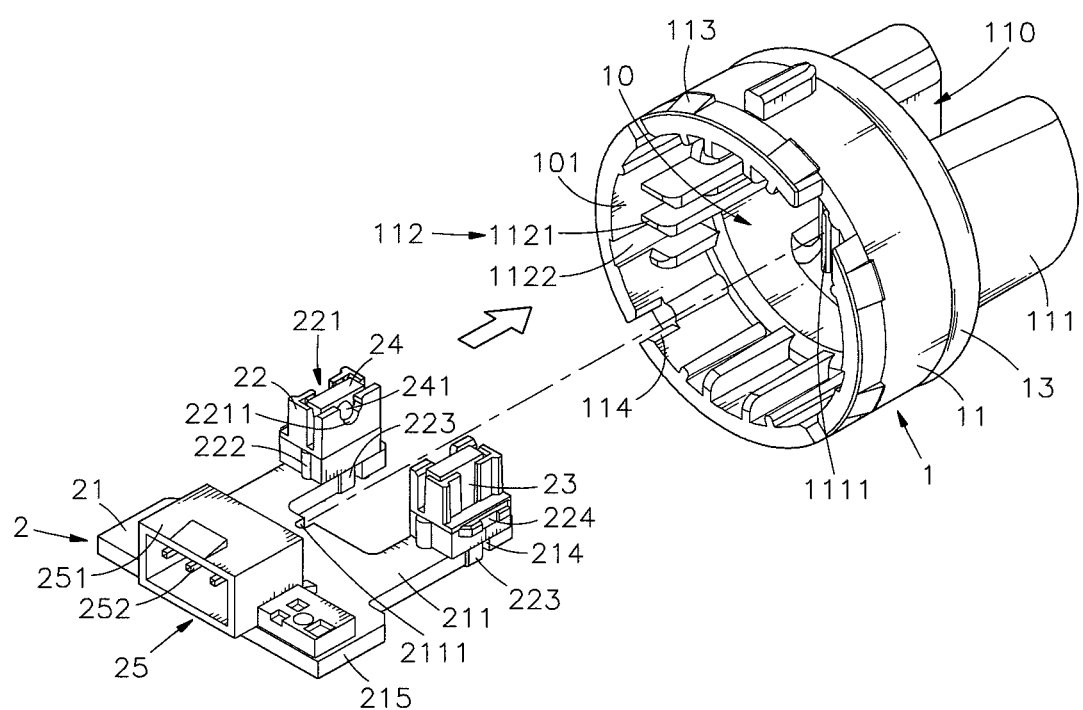
FIG. 7 is an exploded view of a part of the present invention, illustrating the relationship between the sensing module and the body shell of the housing.
Figure 8:
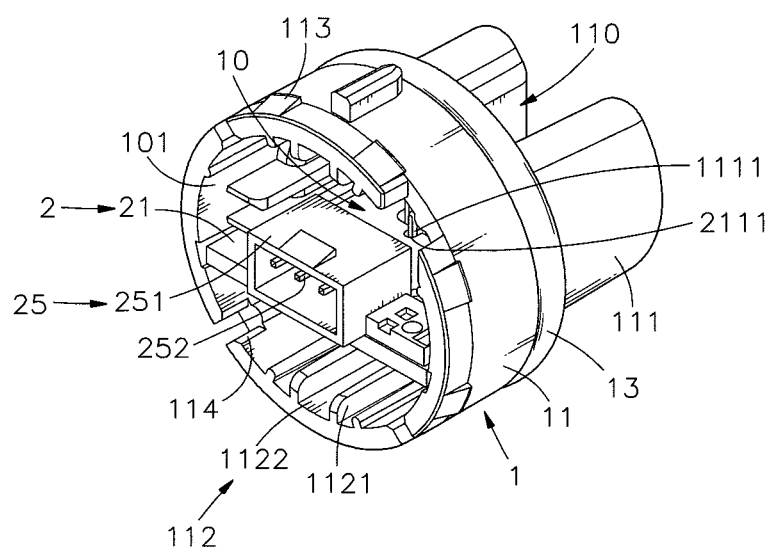
FIG. 8 corresponds to FIG. 7, illustrating the sensing module installed in the body shell of the housing.
Figure 9:
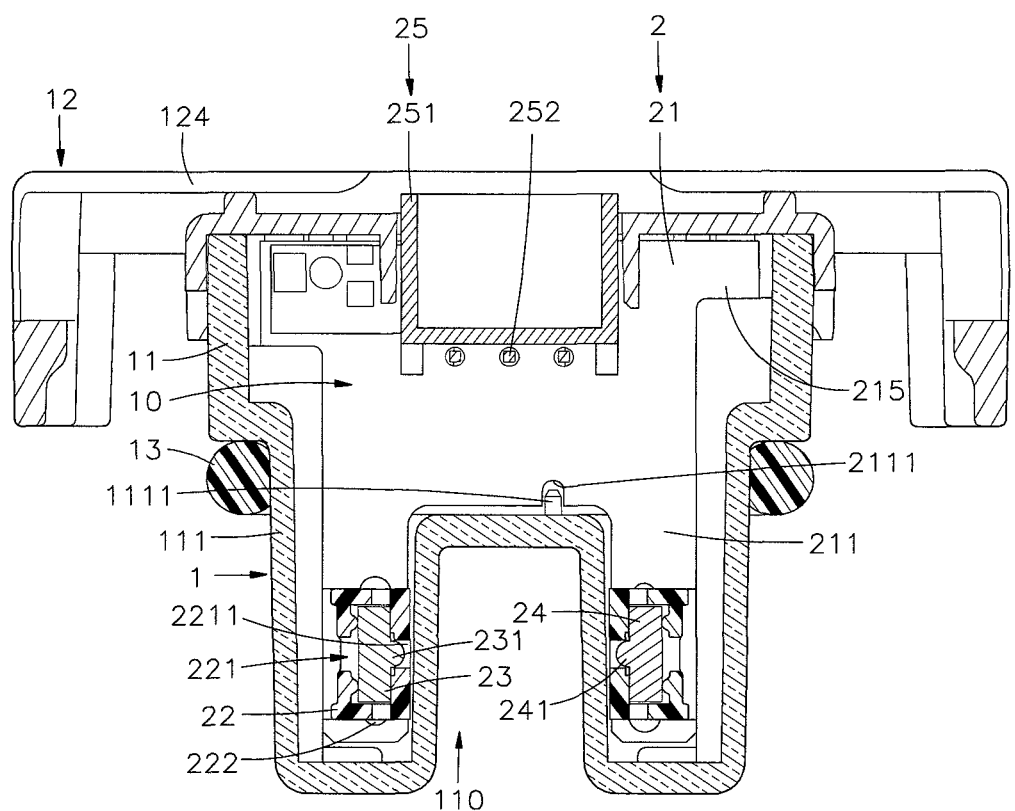
FIG. 9 is a sectional top view of the present invention, illustrating the positioning of the sensing module in the housing.
Figure 10:
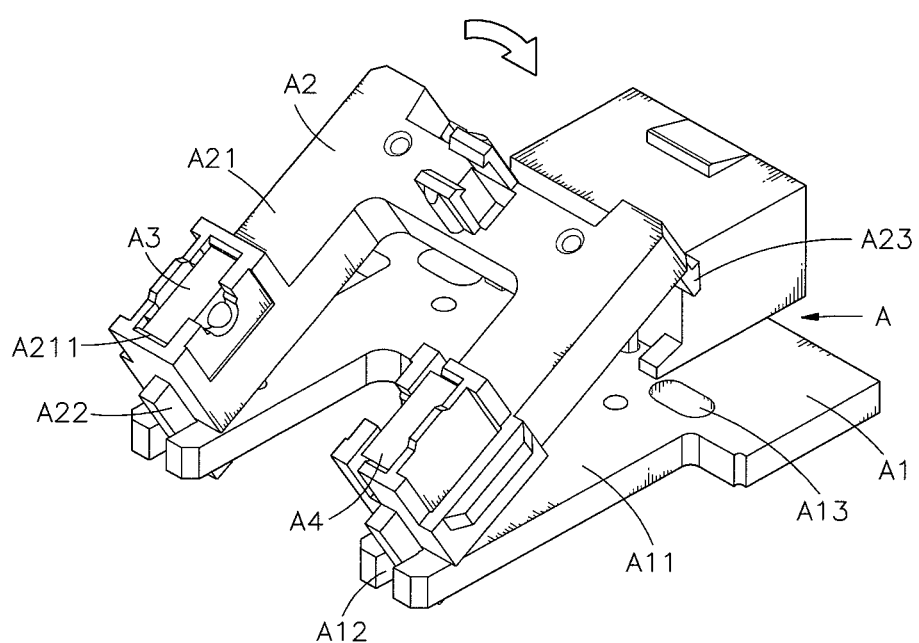
FIG. 10 is a schematic drawing of a water quality sensor according to the prior art.

The body shell 11 further comprises a convex rib 1111 (see FIGS. 7 and 8) disposed inside the accommodation chamber 10 and spaced between the hollow protruding portions 111 at different distances, a positioning structure 112, which comprises a plurality of partition plates 1121 protruded from an inside wall thereof and arranged in pairs and respectively extended to the inside of the hollow protruding portions 111 and a mounting groove 1122 defined in between each pair of partition plates 1121, a plurality of hook blocks 113 located on an outside wall thereof and equiangularly spaced around the opening 101, a position-limiting groove 114 defined between each two adjacent hook blocks 113 around the opening 101, and a plurality of engagement blocks 115 raised from an outside wall thereof and disposed between the hollow protruding portions 111 and the hook blocks 113.

Further, the cover 12 comprises a plurality of hook holes 121 equiangularly spaced from one another corresponding to the hook blocks 113 of the body shell 11, a T-shaped locating block 122 disposed between each two adjacent hook holes 121 corresponding to one respective position-limiting groove 114 of the body shell 11, a plurality of positioning grooves 123 respectively disposed corresponding to the engagement blocks 115 of the body shell 11, two hook type lugs 124 symmetrically extended from two opposite lateral sides thereof and then turned forward toward the body shell 11, and a mounting hole 1241 defined in each hook type lug 124.

The sensing module 2 comprises a circuit board 21, and two connectors 22 mounted at the circuit board 21. The circuit board 21 comprises two positioning plates 211 respectively extended from two opposite lateral sides thereof in a parallel manner, an engaging groove 2111 (see FIGS. 7 and 8) located on a border edge thereof and spaced between the two positioning plate 211 at different distances, a plurality of via holes 212 located on each positioning plate 211 and arranged in line, two position-limiting holes 213 of different diameters located on each positioning plate 211 and disposed at opposing front and rear sides relative to the associating series of via holes 212, two retaining notches 214 located on two opposite lateral sides of each positioning plate 211, and two side plates 215 respectively outwardly extended from the positioning plates 211 at right angles.

Further, each connector 22 of the sensing module 2 comprises a recessed chamber 221 facing upwards, two positioning pins 222 downwardly extended from a bottom wall thereof and respectively disposed at opposing front and rear sides thereof, a top notch 2211 located on the topmost edge of an inner lateral side thereof in communication with the recessed chamber 221, two hook members 223 respectively downwardly extended from two opposite lateral sides of the bottom wall, and a guide rail 224 located at an outer lateral side thereof.

The sensing module 2 further comprises a light emitter 23 and a light receiver 24 respectively mounted in the recessed chambers 221 of the two connectors 22, and a transmission interface 25 mounted on the circuit board 21. Further, the two connectors 22 are mounted on the circuit board 21 in reversed directions with a phase difference of 180 degrees therebetween. The light emitter 23 comprises a light-emitting surface 231 facing toward the top notch 2211 of the respective connector 22, and positive and negative electrode pins 232 located at a bottom side thereof and inserted through a bottom wall of the respective connector 22.

The light receiver 24 comprises a light-receiving surface 241 facing toward the top notch 2211 of the respective connector 22 and the light-emitting surface 231 of the light emitter 23, and positive and negative electrode pins 242 located at a bottom side thereof and inserted through a bottom wall of the respective connector 22. The transmission interface 25 comprises a jack 251, and a plurality of conducting terminals 252 mounted in the jack 251 and respectively electrically bonded to respective contacts (not shown) on the circuit board 21.

The sensing module 2 further comprises a driver circuit or control IC (not shown) installed in the circuit board 21 and adapted for driving the light emitter 23 and the light receiver 24.

Alternatively, the sensing module 2 can be electrically connected to an external driver circuit for driving the light emitter 23 and the light receiver 24. Since the techniques in which how the light emitter and the light receiver are driven to work is of the known art, we shall not repeat them here.

Referring to FIGS. 5-9, when assembling the sensing module 2, use an automatic plug-in apparatus to install the two connectors 22 in the respective positioning plates 211 of the circuit board 21 one after another. During installation, the positioning pins 222 of the connectors 22 are respectively downwardly inserted into the position-limiting holes 213 of the respective positioning plates 211 to guide the electrode pins 232 of the light emitter 23 the electrode pins of the light receiver 24 into the respective via holes 212 on the respective positioning plates 211. As soon as the respective bottom walls of the connectors 22 are abutted against the surfaces of the respective positioning plates 211, the hook members 223 of the connectors 22 are respectively hooked in the respective retaining notches 214 on the respective positioning plates 211. After installation, the connectors 22 are firmly positioned on the respective positioning plates 211 in an upright position and disposed in reversed directions with a phase difference of 180 degrees therebetween. At this time, the light-emitting surface 231 of the light emitter 23 and the light-receiving surface 241 of the light receiver 24 are disposed to face each other. Thereafter, the electrode pins 232 of the light emitter 23 and the electrode pins 242 of the light receiver 24 are respectively electrically bonded to the respective via holes 212 of the circuit board 21 using through-hole-type mounting technology. The two positioning pins 222 of each connector 22 of the sensing module 2 have different diameters fitting the respective position-limiting holes 213 on each positioning plate 211 of the circuit board 21 so that the two connectors 22 can be accurately installed in the two positioning plates 211 of the circuit board 21 with a phase difference of 180 degrees therebetween, avoiding an installation error that can lead to an operational failure of the light emitter 23 and the light receiver 24. The structural design of the connectors 22 allows each connector 22 to selectively receive the light emitter 23 or the light receiver 24, enabling the two connectors 22 to be installed in the circuit board 21 in reversed directions using an automatic plug-in apparatus. Thus, the invention allows the implementation of automated assembly to replace manual assembly, reducing the risk of human error, saving much labor and production costs, improving product quality and increasing product yield. Further, the mold sharing design of the connectors 22 does not need to prepare multiple molds for enabling the connectors 22 to mate with the light emitter 23 and the light receiver 24, saving one half the mold cost, facilitating automatic production, improving the production speed and efficiency, and reducing the manufacturing costs.

After assembling the sensing module 2, insert the circuit board 21 of the sensing module 2 into the accommodation chamber 10 of the body shell 11 of the housing 1 to force the positioning plates 211 of the circuit board 21 and the guide rails 224 of the connectors 22 along the mounting grooves 1122 of the positioning structure 112 into the inside of the hollow protruding portions 111. After the circuit board 21 is set in position, the side plates 215 of the circuit board 21 are respectively stopped in the respective mounting grooves 1122, and the engaging groove 2111 of the circuit board 21 between the two positioning plates 211 is engaged with the convex rib 1111 of the body shell 11. The mating design between the engaging groove 2111 of the circuit board 21 and the convex rib 1111 of the body shell 11 prevents a mounting error between the circuit board 21 and the body shell 11, achieving a foolproof effect.

Thereafter, cap the cover 12 onto the body shell 11 to force the hook holes 121, locating blocks 122 and positioning grooves 123 of the cover 12 into engagement with the respective hook blocks 113, position-limiting grooves 114 and engagement blocks 115 of the body shell 11, enabling the transmission interface 25 of the sensing module 2 to be positioned in the slot 120 of the cover 1, and thus, the sensing module 2 is firmly secured to the housing 1 inside the accommodation chamber 10.

When using the water quality sensor of the present invention in an electric washing appliance (such as laundry washing machine, dishwasher, or any other electric home appliance that needs to use water), mount the housing 1 of the water quality sensor inside the body of the electric washing appliance (not shown) to suspend the two hollow protruding portions 111 in the working area of the electric washing appliance and to force the mounting holes 1241 of the hook type lugs 124 of the cover 12 into engagement with respective parts of the frame of the body of the electric washing appliance. At this time, the waterproof gasket 13 that is mounted on the body shell 11 is abutted against a part of the frame of the body of the electric washing appliance to seal the gap between the working area of the electric washing appliance and the water quality sensor to prevent water from leaking out of the working area. After installation of the sensing module 2 in the electric washing appliance, use a transmission cable to connect the transmission interface 25 to the control system (not shown) of the electric washing appliance for allowing the control system to detect the water quality (such as water turbidity) by means of the light emitter 23 and the light receiver 24.

During the washing operation of the electric washing appliance, cleaning fluid or detergent and the objects to be cleaned (such as clothes or dishes, kitchen utensils, etc.) are contained in the cleaning water in the working area, thus, impurities (such as dust, fines, debris, suspended particulates, or stains) in the cleaning fluid or the objects to be cleaned can cause turbulence. During the operation of the control system of the electric washing appliance, water in the working area of the electric washing appliance is forced to flow through the open passageway 110 between the two hollow protruding portions 111 of the housing 1, and the light emitter 23 of the sensing module 2 is controlled to emit light through the open passageway 110 toward the light receiver 24. When the emitted light passes through water in between the two hollow protruding portions 111, it is scattered, and the light which is not scattered will be captured by the light receiver 24, which produces an electronic signal that is transmitted through the transmission interface 25 to the control system of the electric washing appliance and then converted to a turbidity. Subject to the turbidity measured, the control system can further set the subsequent cleaning procedure to achieve high-efficiency washing performance and the effects of energy-saving and water-saving.

As described above, the sensing module 2 is mounted in the accommodation chamber 10 inside the body shell 11 of the housing 1 with the circuit board 21 and the positioning plates 211 respectively positioned in the hollow protruding portions 111 of the body shell 11; the two connectors 22 are identical in structure and respectively mounted on the two positioning plates 211 of the circuit board 21 with a phase difference of 180 degrees therebetween; the light emitter 23 and the light receiver 24 are respectively mounted in the two connectors 22 to face toward each other for detecting the quality of the water that flows through the open passageway 110 between the two hollow protruding portions 111 of the body shell 11. Thus, the invention allows the implementation of automated assembly to replace manual assembly, reducing the risk of human error, saving much labor and production costs, improving product quality and increasing product yield. Further, the mold sharing design of the connectors of the sensing module does not need to prepare multiple molds for enabling the connectors to mate with the light emitter and the light receiver, saving one half the mold cost, facilitating automatic production, improving the production speed and efficiency, and reducing the manufacturing costs.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A water quality sensor, comprising:
   a housing comprising a body shell and a cover, said body shell comprising two hollow protruding portions extended from a back side thereof, an opening located on an opposite front side thereof and an accommodation chamber defined therein in communication with said opening, said cover being capped on said body shell to close said opening; and
   a sensing module mounted in said accommodation chamber of said housing, said sensing module comprising a circuit board, two connectors mounted on said circuit board in reversed directions with a phase difference of 180 degrees therebetween, a light emitter mounted in one said connector and a light receiver mounted in the other said connector and facing toward said light emitter, said circuit board comprising two positioning plates respectively inserted into the respective said hollow protruding portions of said body shell of said housing and adapted for supporting said two connectors respectively, a plurality of via holes and a plurality of position-limiting holes located on each said positioning plate and arranged in a line and two retaining notches respectively located on two opposite lateral sides of each said positioning plate, each said connector comprising a recessed chamber adapted for accommodating one of said light emitter and said light receiver, a plurality of positioning pins respectively mounted in the said position-limiting holes on one respective said positioning plate, two hook members respectively hooked in the said retaining notches on the respective said positioning plate of said circuit board, said light emitter comprising a light-emitting surface and a plurality of electrode pins downwardly extended out of the respective said connector and electrically connected to the respective via holes on the respective said positioning plate of said circuit board, said light receiver comprising a light-receiving surface facing toward said light-emitting surface of said light emitter and a plurality of electrode pins downwardly extended out of the respective said connector and electrically connected to the respective via holes on the respective said positioning plate of said circuit board,
   wherein said position-limiting holes on each said positioning plate of said circuit board have different diameters and are respectively disposed at opposing front and rear sides relative to the said via holes on the respective said positioning plate; the positioning pins of each said connector have different diameters fitting the respective diameters of the respective said position-limiting holes on the respective said positioning plate of said circuit board.

2. The water quality sensor as claimed in claim 1, wherein said body shell of said housing defines an open passageway between said two hollow protruding portion; said housing further comprises a waterproof gasket mounted around said two hollow protruding portions and abutted against a back wall of said body shell.

3. The water quality sensor as claimed in claim 1, wherein said body shell of said housing body shell further comprises a convex rib disposed inside said accommodation chamber between said two hollow protruding portions; said circuit board of said sensing module further comprises an engaging groove disposed between said two positioning plates and forced into engagement with said convex rib of said body shell of said housing.

4. The water quality sensor as claimed in claim 1, wherein said body shell of said housing further comprises a positioning structure disposed inside said accommodation chamber, said positioning structure comprising a plurality of partition plates protruded from an inside wall thereof and arranged in pairs and respectively extended to the inside of said hollow protruding portions and a mounting groove defined in each pair of said partition plates; said positioning plates of said circuit board of said sensing module are respectively inserted through said mounting grooves between said partition plates and positioned in the respective said hollow protruding portions.

5. The water quality sensor as claimed in claim 1, wherein said body shell of said housing further comprises a plurality of hook blocks located on an outside wall thereof and equiangularly spaced around said opening, a position-limiting groove defined between each two adjacent said hook blocks around said opening; said cover of said housing comprises a plurality of hook holes respectively forced into engagement with the respective hook blocks of said body shell, and a plurality of locating blocks respectively forced into engagement with the respective said position-limiting grooves of said body shell.

6. The water quality sensor as claimed in claim 1, wherein said cover of said housing further comprises a slot cut through opposing front and back walls thereof; said sensing module further comprises a transmission interface mounted on said circuit board and exposed to said slot of said cover of said housing.

7. The water quality sensor as claimed in claim 1, wherein said cover of said housing further comprises two hook type lugs respectively extended from two opposite lateral sides thereof, and a mounting hole defined in each said hook type lug for mounting.

8. The water quality sensor as claimed in claim 1, wherein said connectors of said sensing module are respectively mounted on said positioning plates of said circuit board in an upright position.

9. The water quality sensor as claimed in claim 1, wherein each said connector of said sensing module further comprises a top notch located on the topmost edge of an inner lateral side thereof in communication with said recessed chamber; said light-emitting surface of said light emitter and said light-receiving surface of said light receiver are respectively exposed to the respective said top notches of the respective said connectors to face toward each other.

* * * * *